United States Patent
Cisterni

(10) Patent No.: US 10,012,623 B2
(45) Date of Patent: Jul. 3, 2018

(54) APPARATUS AND METHOD FOR MITIGATION OF ALTERATIONS IN MASS SPECTROMETRY IN THE PRESENCE OF HYDROGEN

(71) Applicant: Marco Cisterni, Bologna (IT)

(72) Inventor: Marco Cisterni, Bologna (IT)

(73) Assignee: Marco Cisterni, Bologna (IT)

( * ) Notice: Subject to any disclaimer, the term of this patent is extended or adjusted under 35 U.S.C. 154(b) by 0 days.

(21) Appl. No.: 15/529,309

(22) PCT Filed: Nov. 20, 2015

(86) PCT No.: PCT/IB2015/058998
§ 371 (c)(1),
(2) Date: May 24, 2017

(87) PCT Pub. No.: WO2016/083964
PCT Pub. Date: Jun. 2, 2016

(65) Prior Publication Data
US 2017/0261475 A1    Sep. 14, 2017

(30) Foreign Application Priority Data
Nov. 24, 2014 (IT) .............................. BO2014A0658

(51) Int. Cl.
*H01J 49/00* (2006.01)
*G01N 30/72* (2006.01)
(Continued)

(52) U.S. Cl.
CPC ......... *G01N 30/7206* (2013.01); *G01N 30/14* (2013.01); *G01N 2030/143* (2013.01);
(Continued)

(58) Field of Classification Search
CPC .............. G01N 30/7206; G01N 30/14; G01N 2030/143; H01J 49/145; H01J 49/0031; H01J 49/147
(Continued)

(56) References Cited

U.S. PATENT DOCUMENTS 2,813,979 A    11/1957 Starr
2,821,662 A    1/1958 Bell et al.
(Continued)

FOREIGN PATENT DOCUMENTS

DE    10 2010 020 933 A1    9/2011
GB    769291    3/1957

OTHER PUBLICATIONS

"Types of Diamond like carbon (DLC)", Retrieved from the Internet: https://web.archive.org/web/20141010235809/http://www.diamondcoating.net/Types_of_hard_carbon.html, Retrieved on Mar. 24, 2016 (2014).

*Primary Examiner* — Michael Maskell
(74) *Attorney, Agent, or Firm* — Jeffrey N. Townes; Cozen O'Connor

(57) ABSTRACT

Gas chromatograph-mass spectrometer comprising an ion source, the walls of which are realized or covered with at least one layer of graphene. Thus realized, the gas chromatograph-mass spectrometer proves to be particularly suited to the analysis samples containing hydrogen in addition to the substances to be analyzed. This situation generally occurs when the mass spectrometer is coupled to a gas chromatograph that utilizes hydrogen as the carrier gas.

20 Claims, 5 Drawing Sheets

(51) Int. Cl.
*G01N 30/14* (2006.01)
*H01J 49/14* (2006.01)

(52) U.S. Cl.
CPC ......... *H01J 49/0031* (2013.01); *H01J 49/145* (2013.01); *H01J 49/147* (2013.01)

(58) Field of Classification Search
USPC ........................................ 250/281, 282, 288
See application file for complete search history.

(56) References Cited

U.S. PATENT DOCUMENTS

| | | | |
|---|---|---|---|
| 5,089,746 A | 2/1992 | Rosenblum et al. | |
| 6,351,983 B1 | 3/2002 | Haas et al. | |
| 2006/0097645 A1 | 5/2006 | Horsky | |
| 2009/0179158 A1* | 7/2009 | Stone | H01J 37/16 250/423 R |
| 2013/0299691 A1* | 11/2013 | Jones | H01J 49/145 250/282 |
| 2015/0204827 A1* | 7/2015 | Duraffourg | G01N 30/7206 250/288 |

\* cited by examiner

APPARATUS AND METHOD FOR MITIGATION OF ALTERATIONS IN MASS SPECTROMETRY IN THE PRESENCE OF HYDROGEN

CROSS-REFERENCE TO RELATED APPLICATIONS

This application is a national-stage application under 35 U.S.C. § 371 of International PCT Application No. PCT/IB2015/058998, filed Nov. 20, 2015, which claims priority to Italian Patent Application No. BO2014A000658, filed Nov. 24, 2014, both of which are hereby incorporated by reference in their entirety.

The present invention refers in general terms to a gas chromatograph-mass spectrometer (GG-MS system) comprising an ion source, the walls of which are realized or covered with at least one layer of graphene. Thus realized, the gas chromatograph-mass spectrometer proves to be particularly suited to the analysis of samples containing hydrogen in addition to the substances to be analysed. This situation generally occurs when the mass spectrometer is coupled to a gas chromatograph that utilizes hydrogen as the carrier gas.

STATE OF THE ART

Mass spectrometers (MS) are analytical instruments that are frequently coupled, with the function of detectors, to a gas chromatograph (GC-MS system). In a mass spectrometer, the ion source serves to receive the substances to be analyzed, ionize them and send them—after they have been ionized and fragmented—to the other components of the spectrometer. The ion source is made up of an ionization chamber, inside of which a beam of electrons emitted by a heated filament flows through the gas to be ionized and impinges on a collector and from a system for acceleration of the ions produced in the chamber.

In the ion sources most used, ionization takes place using electron ionization (EI) or chemical ionization (CI). In an electron ionization (EI) ion source, a beam of electrons (emitted by an incandescent metal filament) passes through the chamber colliding with the substance to be analyzed contained in the same chamber, bringing about the ionization and fragmentation thereof. In a chemical ionization ion source, ionization of the substance to be analyzed is instead mediated by the presence of a reagent gas (generally methane or ammonia); the reagent gas, which is ionized by impact with a beam of electrons, interacts with the substance to be analyzed, causing, in turn, the ionization thereof, but generally not the fragmentation thereof.

FIG. 1 is a scheme of an ionization chamber for an electron ionization (EI) ion source of the prior art. The ionization chamber is delimited by side walls (L) and by a wall (P) from which the ions produced in the chamber exit through an opening. The substances to be analyzed reach the chamber, where they are ionized and fragmented by means of a beam (A) of electrons emitted by a filament (F) and collected by a collector (C). The ions thus produced are accelerated towards the perforated bottom wall (P) by the electrostatic field produced by the electrode (R) called the "repeller". In the case of the scheme shown in FIG. 1, the wall (P) is realized separately from the side walls (L) and it is joined to them when the ion source is assembled for normal operation. The same holds for the repeller (R). The ions exiting from the wall (P) pass through the other components of the ion source, i.e., electrostatic lenses, etc., which are not indicated in the figure, and subsequently reach the other parts of the mass spectrometer, where they are detected.

The walls of ionization chambers for ion sources, being electron or chemical ionization ion sources, are normally realized using electrically and thermally conductive materials, such as stainless steel for example. These materials meet certain requirements, including: stability at operating temperature, chemical inertness and electrical and thermal conductivity.

Covering the internal walls of ion sources with various materials for the purpose of improving the performance thereof is known in the field of mass spectrometry.

For example, U.S. Pat. No. 769,291 discloses an ion source comprising parts made of graphite that permit rapid recovery of the contaminating substances that deposit on the walls of the source during use. U.S. Pat. No. 2,821,662 discloses a variant of the same mass spectrometer, which is capable of operating at high ionization temperatures (1500°-3000° C.), and in which the ion source comprises a graphite block having a particular geometry.

Graphene has also been used to cover the evaporation plate in mass spectrometers that utilize MALDI-TOF technology, so as to improve the resolution of the isotopes of substances with low molecular weights, as disclosed in patent DE 10 2010 020 933.

US patent application 2013/0299691 discloses a mass spectrometer in which the ion source is covered by various materials, for example metallic carbides and metallic borides, ceramic materials or DLC (Diamond-like carbon), an amorphous carbon material, for the purpose of preventing or limiting contamination of the surfaces of the chamber.

When hydrogen is present inside the ion source and the walls are made of metal, problems can arise due to undesirable interactions between the hydrogen and the ions produced in the ionization chamber. The typical situation in which this occurs is found in the case of an ion source of a mass spectrometer, utilized with a gas chromatograph in which hydrogen is the carrier gas (GC-MS system using $H_2$ carrier gas).

Compared to other gases, such as helium for example, hydrogen as the carrier gas offers considerable advantages, in terms of performance, cost and availability. However, it has been observed that several problems related to the presence of hydrogen can arise in GC-MS systems.

Firstly, the spectra acquired by the mass spectrometer prove to be altered for some substances, particularly for those organic substances that have bonds or functional groups that can be reduced in the presence of hydrogen. It has been observed that the extent of alteration also depends upon the concentration of the substance in the sample analysed. This phenomenon makes qualitative analysis of a sample of unknown composition difficult and in some cases impossible, for the mass spectrum obtained differs from the spectrum expected for that substance.

Moreover, the peaks of some substances lose resolution, exhibiting "tails", which also make quantitative analysis of the substance difficult.

Additionally, there is reduced sensitivity and linearity of the spectrometer, especially for substances present in small quantities. The extent of the alterations in the spectrum of some substances is often such as to undermine use of hydrogen as the carrier gas in GC-MS systems.

A solution currently being proposed to reduce the problems created by hydrogen in GC-MS systems consists in using a bottom wall of the ion source with a hole of a larger diameter. However, this solution mitigates, without completing resolving, the problem of "tails" appearing after the peaks of the principal substances, while it has no effect on the alteration of the spectrum owing to the reduction of bonds and functional groups. Moreover, the wider hole causes a decrease in the sensitivity of the instrument, leading to worse performance of the instrument.

Therefore, in this sector, the problem of devising a method for mitigation or elimination of alterations of the mass spectrum of substances when the spectrum is detected in the presence of hydrogen remains, as does the problem of devising a mass spectrometer capable of implementing this method.

SUMMARY OF THE INVENTION

In a first aspect, the present invention refers to a gas chromatograph-mass spectrometer (hereinafter "GC-MS system"), characterized in that the ion source of the mass spectrometer comprises an ionization chamber in which the internal surface of at least one wall of said ionization chamber has the chemical structure of at least one layer of graphene.

In an additional aspect, the present invention refers to a gas chromatography-mass spectrometry method (hereinafter "GC-MS method") comprising:
providing a first sample comprising a plurality of analytes;
providing a separation column comprising at least one stationary phase capable of selectively adsorbing at least one analyte;
introducing the first sample at one end of the separation column and enabling the sample to flow through the column, separating said plurality of analytes based on their affinity for said stationary phase, utilizing hydrogen as the carrier gas, thereby obtaining at least a second gaseous sample;
ionizing said second gaseous sample in the ion source of a mass spectrometer comprising an ionization chamber in which the internal surface of at least one wall of said ionization chamber has the chemical structure of at least one layer of graphene, producing ions;
analyzing the ions produced based on the mass thereof.

In a further aspect, the present invention refers to a mass spectrometry method comprising:
providing a gaseous sample comprising hydrogen and at least one analyte;
ionizing said gaseous sample in the ion source of a mass spectrometer comprising an ionization chamber in which the internal surface of at least one wall of said ionization chamber has the chemical structure of at least one layer of graphene, producing ions;
analyzing the ions produced based on the mass thereof.

DETAILED DESCRIPTION OF THE INVENTION

The invention shall be explained in detail below with reference also to the attached figures, of which:

Figure 4:
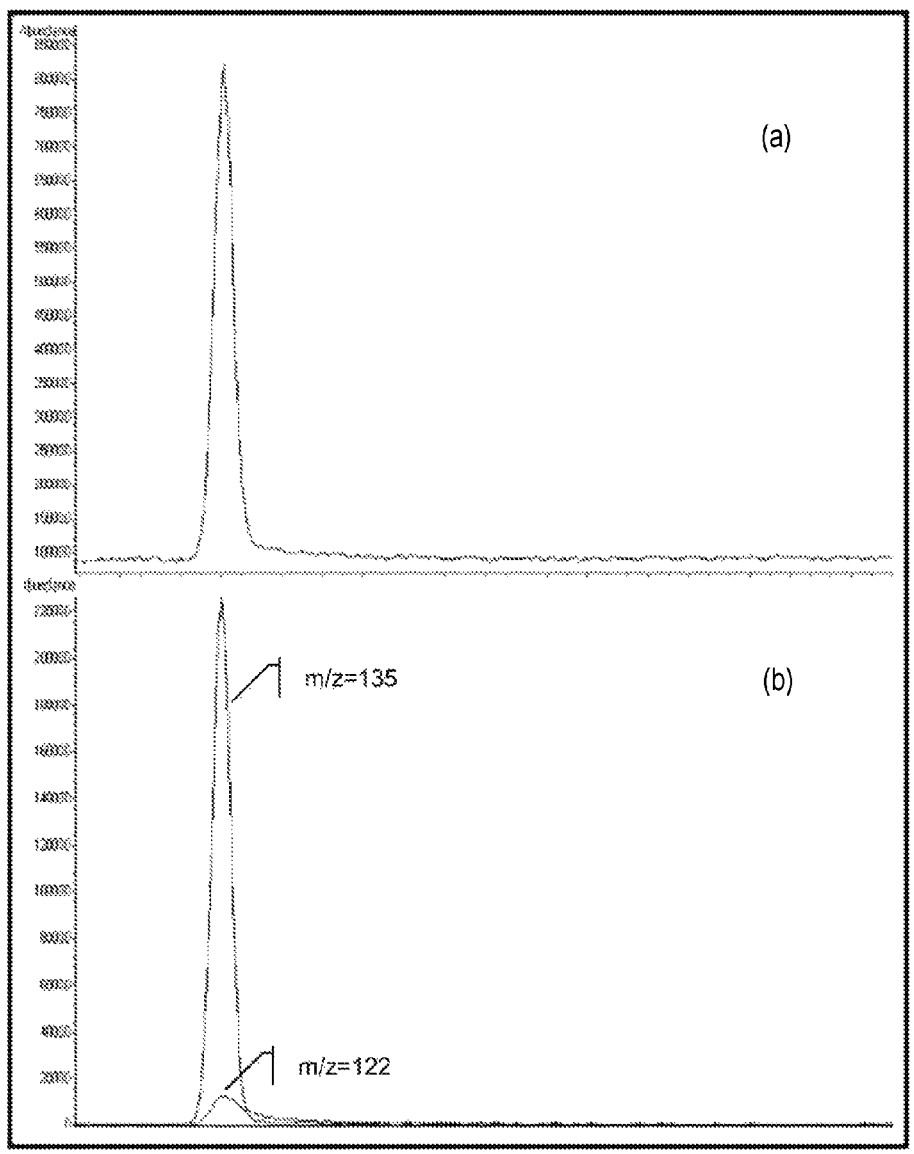
Figure 5:
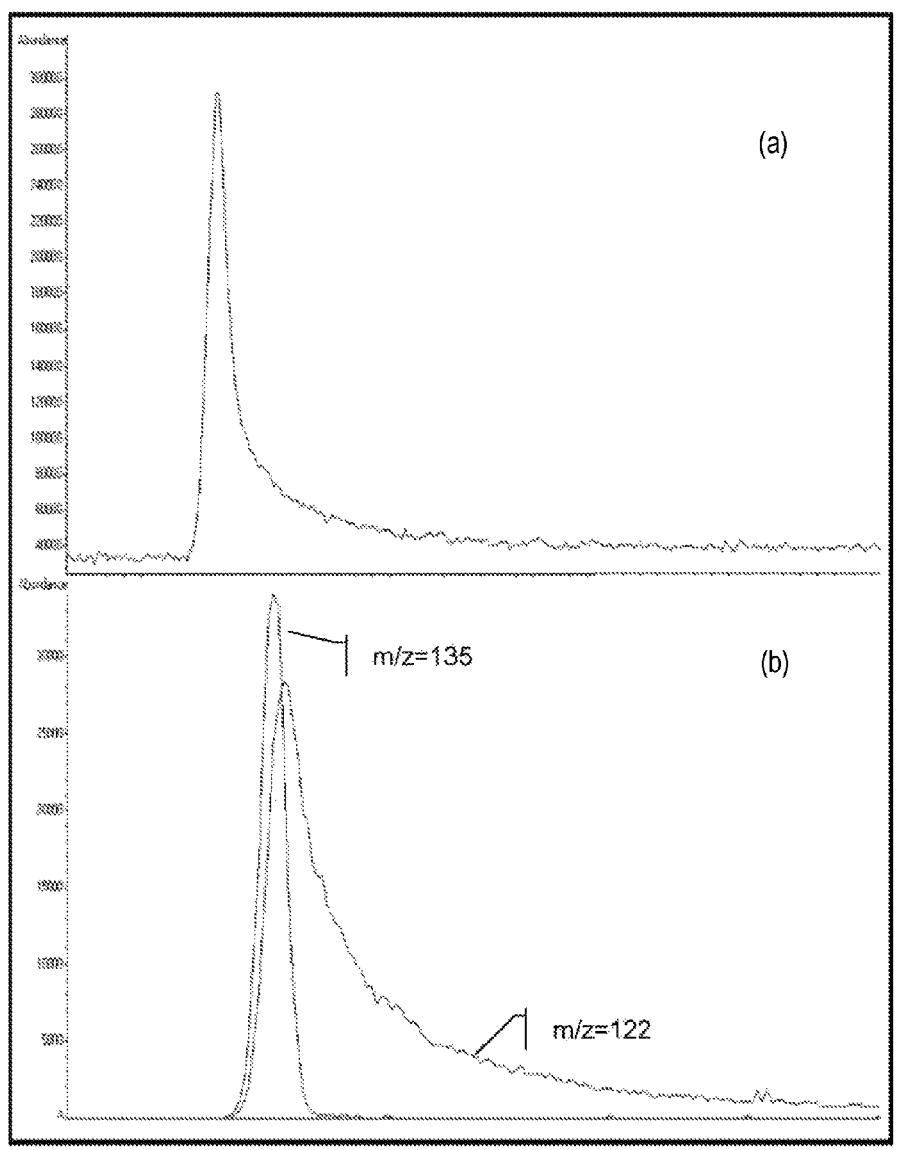
Figure 6:
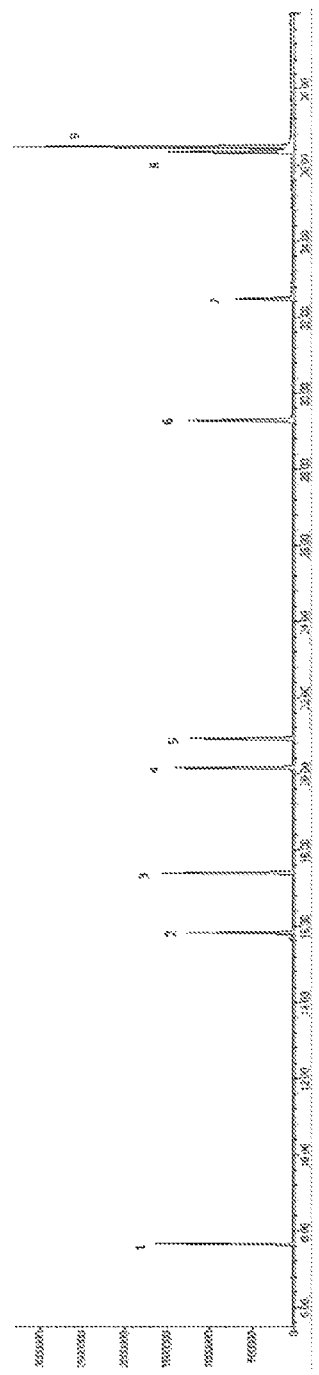
Figure 7:
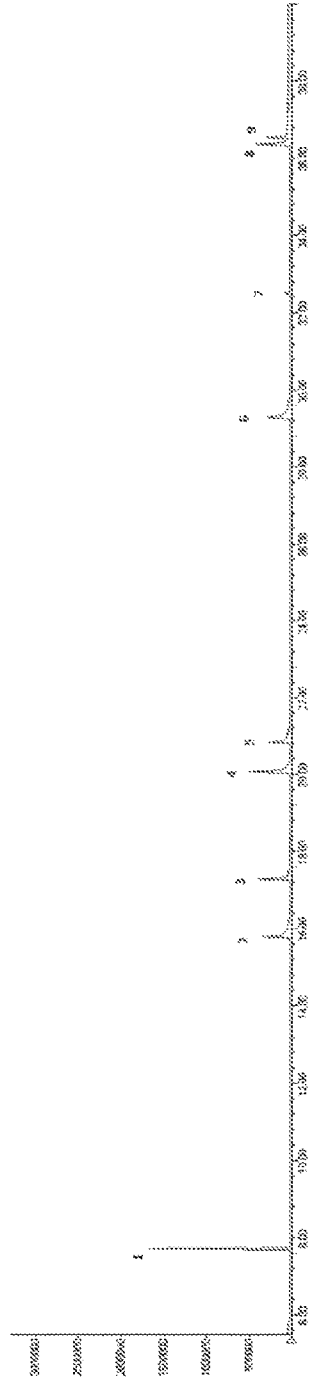
Figure 8:
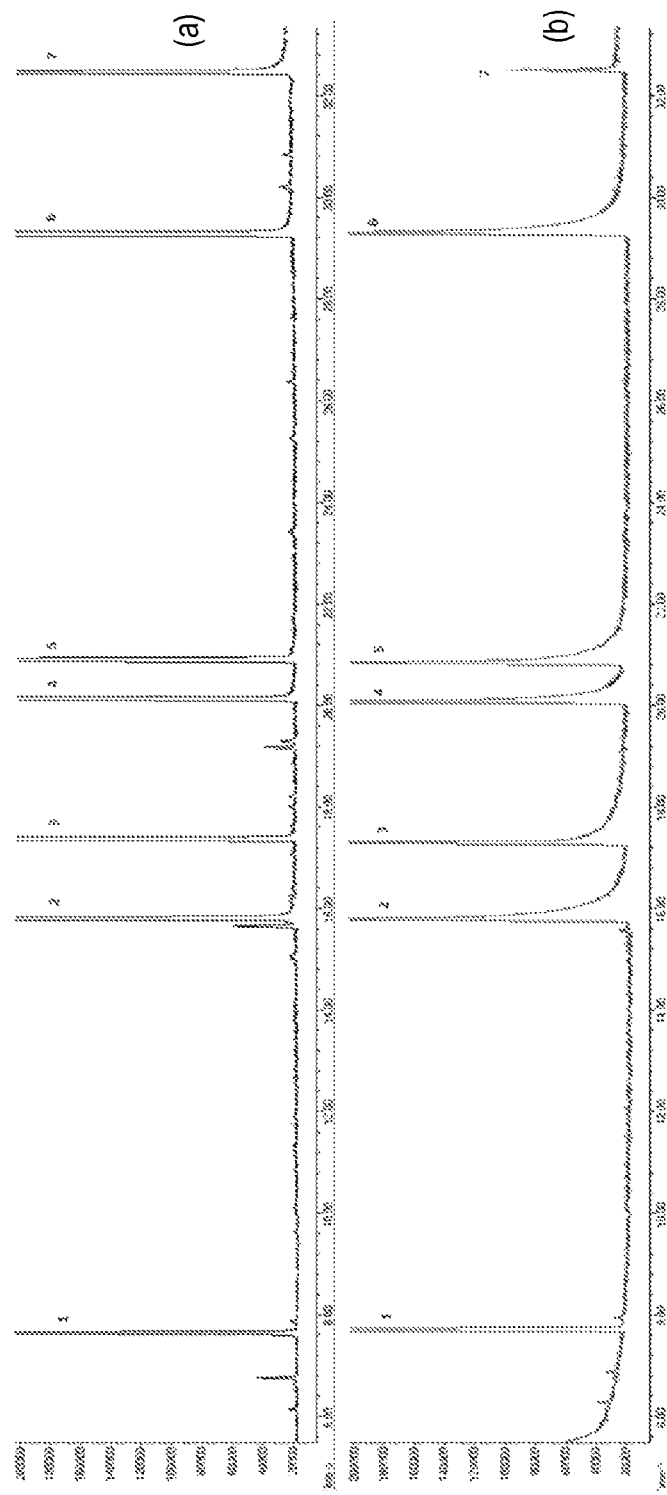

FIG. 4(*a*): Total Ion Current Chromatogram (TIC Chromatogram) of anisaldehyde, obtained using the GC-MS system according to the invention;

FIG. 4(*b*): Extracted Ion Chromatogram (EIC) derived from the Chromatogram shown in FIG. 4(*a*), extracting the ions at m/z 122 and m/z 135;

FIG. 5(*a*): TIC Chromatogram of anisaldehyde, obtained using a conventional GC-MS system;

FIG. 5(*b*): EIC derived from the Chromatogram shown in FIG. 5(*a*), extracting the ions at m/z 122 and m/z 135;

FIG. 6: TIC Chromatogram of the sample for Example 3, obtained using the GC-MS system according to the invention;

FIG. 7: TIC Chromatogram of the sample for Comparison Example 4, obtained using a conventional GC-MS system;

FIG. 8: enlargement of a portion of the chromatogram appearing in FIG. 6 (8(*a*)) and in FIG. 7 (8(*b*)).

In a first aspect, the present invention refers to a gas chromatograph-mass spectrometer (GC-MS system), characterized in that the ion source of the mass spectrometer comprises an ionization chamber in which the internal surface of at least one wall of said ionization chamber has the chemical structure of at least one layer of graphene.

The term "internal surface" or "internal layer" refers to the surface (or layer) that is found, inside an ionization chamber, in direct contact with the gaseous sample to be analysed.

According to a first variant embodiment, the ion source can be selected from among an electron ionization (EI) ion source and a chemical ionization (CI) ion source.

The present invention is described herein below referring to the scheme of the ionization chamber appearing in FIG. 1, which refers to an electron ionization (EI) chamber. For persons skilled in the art, it is clear that various modifications concerning the shape and details of the ionization chamber can be made without departing from the scope of the invention as defined by the claims.

Figure 1:
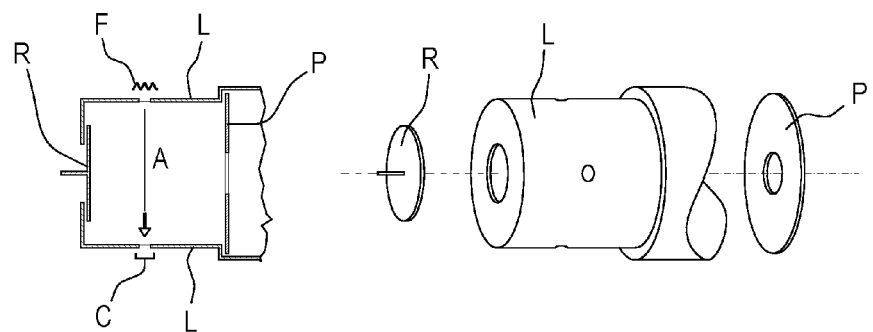
FIG. 1 is a scheme of an ionization chamber for an electron ionization (EI) ion source.

With reference to the scheme appearing in FIG. 1, the at least one wall of the ionization chamber, the internal surface of which has the chemical structure of at least one layer of graphene, can consist of the side wall (L) and/or the wall (P) and/or the repeller (R).

Preferably, the at least one wall of the ionization chamber, the internal surface of which has the chemical structure of at least one layer of graphene, can consist of the side wall (L). According to a further variant, said wall can consist of the side wall (L) and the wall (P). More preferably, the at least one wall of said ionization chamber, the internal surface of which has the chemical structure of at least one layer of graphene, can consist of the side wall (L), the wall (P) and the repeller (R), that is, the internal surface of all the walls of the ionization chamber has the chemical structure of at least one layer of graphene.

According to the present invention, the internal surface of at least one wall of the ionization chamber comprised in the mass spectrometer is realized in such a manner as to minimize contact between the ions and the gases present in the chamber and the metallic walls of the chamber itself, utilizing a material that does not give rise to the problems cited hereinabove and that possesses the required characteristics of stability at the operating temperature, inertness and conductivity.

Therefore, the internal surface of at least one wall of the ionization chamber with which the ions and gases present therein come into contact, has a continuous structure of at least one layer of graphene, with the exception of any impurities or imperfections that may be present depending upon the material employed and the process with which said layer is realized.

According to the definition indicated in the *Gold Book of the International Union for Pure and Applied Chemistry* (IUPAC), the "layer of graphene" is "a single carbon layer of the graphite structure". As is well known, graphite, in turn, is constituted by a plurality of layers of graphene arranged side by side. A "layer of graphite" is thus a layer of graphene. The at least one layer of graphene is a crystalline material, that is, having a structure with a long-range order.

According to a first embodiment, the present invention refers to a GC-MS system, characterized in that the ion source of the mass spectrometer comprises an ionization chamber in which the internal surface of at least one wall of said chamber can have at least one layer of graphene deposited or grown on said at least one surface.

According to this embodiment, at least one layer of graphene is deposited or grown on the internal surface of at least one wall of the ionization chamber using techniques and apparatuses known to the person skilled in the art, such as deposition of graphene from dispersions or liquid solutions, or CVD (Chemical Vapor Deposition) for example.

It should be taken into consideration that preferably no areas should remain uncovered, and therefore, the at least one layer of graphene must be a continuous layer, preferably deposited on the internal surface of all the chamber walls. Moreover, the at least one layer of graphene must withstand the operating temperature of the ion source without altering itself significantly, and it must not release substances inside the ionization chamber that can interfere with normal operation of the source itself.

The at least one layer of graphene grown or deposited on the internal surface of at least one wall of the ionization chamber can be of a thickness less than or equal to 500 nm, preferably less than or equal to 300 nm, and more preferably within the range of 70-100 nm.

This embodiment of the invention proves to be particularly advantageous in that it makes it possible to modify the ionization chamber of a gas chromatograph-mass spectrometer, preferably with an electron (EI) or chemical (CI) ionization ion source, already present on the market.

Furthermore, as the deposition or growth of the at least one layer of graphene can be repeated, the at least one layer of graphene can be restored when the latter undergoes morphological or physico-chemical changes due to use.

According to a further embodiment, the present invention refers to a GC-MS system, characterized in that the ion source of the mass spectrometer comprises an ionization chamber in which the internal surface of at least one wall of said ionization chamber has the structure of graphite.

Graphite is a crystalline material that can be selected from among "crystalline flake graphite" (i.e., with very fine flakes), "microcrystalline" graphite (also called "amorphous graphite"), expanded graphite, pyrolytic graphite and synthetic graphite.

According to a first variant, at least one wall of the ionization chamber is entirely made up of graphite. Graphite not only has the necessary requirements of electrical and thermal conductivity, chemical inertness and resistance to heat, but also the mechanical strength requirements needed to be utilized in the realization of at least one wall of the ionization chamber. The thickness of the at least one wall made up of graphite much be such as to enable assembly of the ionization chamber and the ion source.

In a preferred embodiment, the at least one wall made up of graphite is the wall (P) and/or the repeller (R) of the ionization chamber.

According to an additional variant, the GS-MS system is characterized in that the ion source of the mass spectrometer comprises an ionization chamber in which at least one wall of said chamber has a multilayer structure comprising at least one external metallic layer, preferably in stainless steel, and an internal layer of graphite.

According to a further embodiment, the internal surface of at least one wall of the ionization chamber is covered with an insert, the internal surface of which has the chemical structure of at least one layer of graphene.

According to a preferred variant, said insert can be entirely made up of graphite.

Alternatively, said insert can comprise an internal layer entirely made up of graphite and at least one external support coupled to said internal layer and realized in a material differing from graphite, preferably in stainless steel or in another material known in the prior art for realizing the walls of an ionization chamber.

According to an alternative variant, the internal surface of said insert has at least one layer of graphene deposited or grown on said surface, said insert being realized in a material differing from graphite, preferably in stainless steel.

The thickness of the wall of the insert must be the minimum possible thickness enabling acceptable sturdiness of the piece—which is not subject to mechanical stress during normal operation of the ion source—without altering the operation of the source by excessively reducing the internal volume thereof.

Preferably, the thickness of the wall of the graphite insert can be less than or equal to 2.5 mm; more preferably the thickness can range between 0.4 and 1.5 mm. In the case of thicknesses of less than 0.4 mm, the structural stability of the insert may prove to be jeopardized.

This additional embodiment also enables modification of the ionization chamber of a conventional mass spectrometer in which the walls of the ionization chamber are realized in any material, preferably in stainless steel. The geometry (shape and dimensions) of the insert is therefore generally determined by the geometry of the ionization chamber that is being modified.

In one embodiment, an insert is realized for insertion inside the ionization chamber and it can be made up of one or more parts. The insert must be constructed in such a manner as to entirely cover the metallic walls, so as to prevent contact between the latter and the ions and gases present inside the chamber. Therefore, preferably all the walls of the ionization chamber are covered by said insert. In this manner, the internal surface of the wall of the ionization chamber—the wall with which ions and gases present therein come into contact—is in fact made up of graphite or has at least one layer of graphene deposited or grown thereon.

Moreover, the insert should be replaceable, that is, removable from the chamber, to be replaced and inserted again, for prolonged use of the ion source leads to an accumulation of residue on the internal walls of the source itself.

The use of a removable insert offers the advantage of facilitating maintenance of the ion source, in addition to reducing maintenance time.

It is also possible to select different solutions for the various walls within the same ionization chamber, thereby combining the various embodiments illustrated hereinabove.

Figure 2:
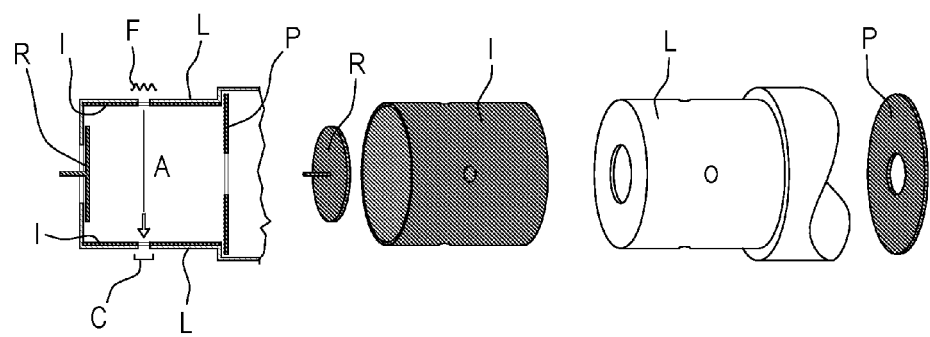
FIG. 2 is a scheme of an embodiment of the ionization chamber of the GC-MS system according to the invention.

According to a specific embodiment, the present invention refers to a GC-MS system characterized in that the ion source of the mass spectrometer comprises an ionization chamber in which the wall (P) is entirely made up of graphite and the wall (L) is entirely covered by a graphite insert. Preferably, the repeller (R) is also entirely made up of graphite. This specific embodiment is illustrated in FIG. 2.

Figure 3:
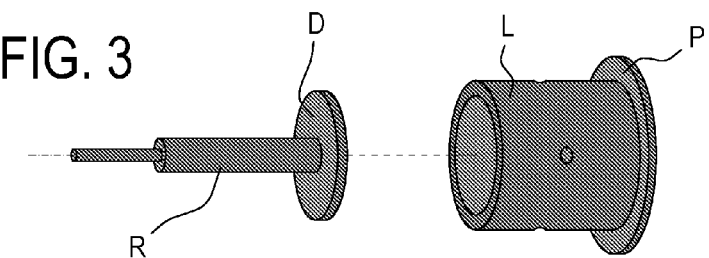
FIG. 3 is a scheme of an embodiment of the ionization chamber of the GC-MS system according to the invention, and used for acquisition of the spectra in Example 3.

The side wall (L) and the wall (P) can be part of a single graphite insert, as illustrated in FIG. 3, in which the side wall (L) of the insert entirely covers the internal wall of the ionization chamber and the wall (P) of the insert substitutes the wall (P) of the ionization chamber.

According to a further specific embodiment, the present invention refers to a GC-MS system characterized in that the ion source of the mass spectrometer comprises an ionization chamber in which the internal surface of the wall (P) has at least one layer of graphene deposited or grown on said surface and the wall (L) is entirely covered by a graphite insert. Preferably, the internal surface of the repeller (R) also has at least one layer of graphene deposited or grown on said surface.

According to a further specific embodiment, the present invention refers to a GC-MS system characterized in that the ion source of the mass spectrometer comprises an ionization chamber in which the wall (P) is entirely made up of graphite and the internal surface of the wall (L) has at least one layer of graphene deposited or grown on said surface. Preferably, the repeller (R) is also entirely made up of graphite.

The GC-MS system according to the invention makes it possible to mitigate alterations of the spectra of organic substances when hydrogen, in addition to the gaseous sample containing the analyte, is present inside the ion source, that is, when hydrogen is employed as the carrier gas in gas chromatography.

The ion source present in mass spectrometers known in the prior art is generally made of metal. Hydrogen has the property of being adsorbed on the surface of many metals. With transition metals for example, it forms interstitial hydrides, in which it occupies empty spaces in the metal lattice. The hydrogen adsorbed on these metals is dissociated into atoms (or in any case, the $H_2$ molecules exhibit great loosening of the bond), and under these conditions it becomes much more reactive. Striking against the walls of the ionization chamber, the more reactive ions in the ionization chamber of a conventional mass spectrometer can react with the hydrogen adsorbed on these walls. There are different factors influencing the reactivity of the ions and the fragment ions: steric strain, presence of aromatic rings, etc.

As they strike the side walls (L) of the ionization chamber, particularly reactive ions can react with the hydrogen adsorbed there, thus modifying their subsequent fragmentation and giving rise to alterations in the mass spectrum of the substance. Other, generally less reactive ions can react more slowly with the hydrogen following impact with the wall (P) towards which they are pushed, released from the metal following the reaction, giving rise to the tail observed after the peak of the substance. Lastly, some ions do not react at all with the hydrogen.

This phenomenon is drastically reduced or eliminated in the GC-MS system according to the invention.

In an additional aspect, the present invention thus refers to a gas chromatography-mass spectrometry method (hereinafter "GC-MS method") comprising the use of the GC-MS system according to the invention as described hereinabove.

In particular, the present invention also refers to a GC-MS method that can comprise:
  providing a first sample comprising a plurality of analytes;
  providing a separation column comprising at least one stationary phase capable of selectively adsorbing at least one analyte;
  introducing the first sample at one end of the separation column and enabling the sample to flow through the column, separating said plurality of analytes based on their affinity for said stationary phase, utilizing hydrogen as the carrier gas, thereby obtaining at least a second gaseous sample;
  ionizing said second gaseous sample in the ion source of a mass spectrometer comprising an ionization chamber in which the internal surface of at least one wall of said ionization chamber has the chemical structure of at least one layer of graphene, producing ions;
  analysing the ions produced based on the mass thereof.

The GC-MS method according to the invention, in which the ionization of the gaseous sample comprising a plurality of analytes takes place in an ion source having the characteristics described hereinabove, makes it possible to resolve the problems related to undesirable reactions between the hydrogen present in the ionization chamber, together with the at least one analyte, and the ions produced in the ion source, without giving rise to other drawbacks.

The method according to the invention thus proves to be particularly suited to the analysis of a first gaseous sample comprising hydrogen and a plurality of analytes, in which at least one of said analytes is selected from among hydrocarbons ranging from C1 to C50 and having at least one functional group that is reactive to hydrogen. Preferably, said hydrocarbons can be selected from among unsaturated hydrocarbons and/or hydrocarbons containing at least one atom of O, N, S, Cl, F, or P.

In a further aspect, the present invention refers to a mass spectrometry method comprising:
  providing a gaseous sample comprising hydrogen and at least one analyte;
  ionizing said second gaseous sample in the ion source of a mass spectrometer comprising an ionization chamber in which the internal surface of at least one wall of said ionization chamber has the chemical structure of at least one layer of graphene, producing ions;
  analysing the ions produced based on the mass thereof.

The mass spectrometry method also proves to be particularly suited to the analysis of gaseous samples comprising hydrogen and at least one analyte selected from among hydrocarbons ranging from C1-050 and having at least one functional group that is reactive to hydrogen. Preferably, said hydrocarbons can be selected from among unsaturated hydrocarbons and/or hydrocarbons containing at least one atom of O, N, S, Cl, F, or P.

EXAMPLE 1

In a GC-MS system present on the market, the stainless steel internal surface of the walls (L) and (P) of an ionization chamber having the following characteristics:
  cylindrical shape;
  inner diameter of 13.5 mm;
  length of 14 mm;
  wall (P): realized by means of a plate of a diameter of 18 mm, a thickness of about 0.4 mm, with a central hole of a diameter of 3 mm; it is an independent piece with respect to the other walls (L) of the chamber, and it is joined to them when the source is assembled for normal operation;
was modified as illustrated in FIG. 2:

the wall (P) was replaced with a perforated plate (P') entirely made up of graphite, having the same dimensions and equal hole as the wall (P);

an insert (I) entirely made of graphite, with a hollow, cylindrical shape, and a thickness of about 1.0 mm was inserted inside the ionization chamber so as to cover the metallic walls (L);

the repeller (R) was replaced with a repeller (R') in graphite.

The GC-MS system thus modified was employed for the acquisition of a chromatogram of p-Anisaldehyde (4-Methoxybenzaldehyde, CAS:123-11-5) appearing in FIG. 4, injecting a p-Anisaldehyde solution at 500 ppm weight/weight in diethyl ether, and using hydrogen as the carrier gas, under the following conditions:

| | |
|---|---|
| Carrier | $H_2$ - 1 ml/min, constant flow |
| Injection vol. | 1.0 μl |
| Injector | split 1:50 (260° C.) |
| Column | WAX stationary phase, film thickness 0.25 μm inner diameter 0.25 mm; length 60 m |
| Oven | 180° C. (isotherm) |

FIG. 4(a) shows the overall chromatogram for all the ions acquired; FIG. 4(b) shows the plots for the fragment ions with m/z 135 and m/z 122.

COMPARATIVE EXAMPLE 2

The chromatogram in FIG. 5 shows the peak of p-Anisaldehyde (4-Methoxybenzaldehyde, CAS:123-11-5), as acquired with the GC-MS system employed in. Example 1 prior to modification of the ionization chamber, using hydrogen as the carrier gas and the same conditions specified for Example 1.

FIG. 5(a) shows the overall chromatogram for all the ions acquired, where an evident peak tail can be noted. The spectrum observed at the start of the peak is in fact that of anisaldehyde, whereas in the tail the spectrum is different and it is the spectrum typical of p-Cresyl methyl ether (4-Methoxytoluene, CAS: 104-93-8).

FIG. 5(b) contains the plots only for the fragment ions with m/z 135 (typical of anisaldehyde, absent in para-Cresyl methyl ether) and m/z 122 (typical of para-Cresyl methyl ether, absent in anisaldehyde). The extraction of the two ions clearly shows the formation of para-Cresyl methyl ether inside the ionization chamber and its subsequent slow release. Note that the peak relative to p-Cresyl methyl ether is delayed, with respect to the peak of anisaldehyde and it is responsible for the tail.

From a comparison with the spectrum shown in FIGS. 4a and 4b, it can be noted that by using a GC-MS gas chromatograph according to the invention, peak tailing is almost eliminated and the peak of the fragment ion at m/z 122 (typical of p-Cresyl methyl ether) is almost totally eliminated, thereby demonstrating the effectiveness of the solution employed.

EXAMPLE 3

A sample having the composition reported in Table 1, diluted to 3.3% (p/p) in diethyl ether, was analyzed using the GC-MS system according to the invention as described herein below, under the operating conditions reported in Table 2.

The ion source of the GC-MS system was modified as reported in FIG. 3. A cylindrical insert in graphite L was realized, having walls of a thickness of 1 mm, an outer diameter of 13.3 mm and a height of 10 mm. The cylinder is provided with holes for the beam of electrons and for entry of the sample. A bottom wall P was coupled to the cylinder; it was realized entirely in graphite, with a thickness of 0.4 mm and a diameter of 18.5 mm, and it was also provided with a hole for the exit of the ionized sample. The steel repeller present on the instrument was replaced with a repeller R realized entirely in graphite, in which the disc D has a diameter of 11 mm and a thickness of 1 mm.

TABLE 1

| | Substance | % (p/p) |
|---|---|---|
| 1. | Limonene | 10 |
| 2. | Benzoic aldehyde | 10 |
| 3. | Isobornyl acetate | 10 |
| 4. | Styralyl acetate | 10 |
| 5. | Benzyl acetate | 10 |
| 6. | 4-Methoxybenzaldehyde | 10 |
| 7. | 4-Allyl-2-methoxyphenol | 10 |
| 8. | α-Hexylcinnamaldehyde | 10 |
| 9. | Diethyl phthalate | 20 |

TABLE 2

| | |
|---|---|
| Carrier | $H_2$ - 1 ml/min, constant flow |
| Injection vol. | 1.0 μl |
| Injector | split 1:200 (260° C.) |
| Column | WAX stationary phase, film thickness 0.25 μm inner diameter 0.25 mm; length 60 m |
| Thermal ramp | Start: 80° C., hold 5 min. Ramp 1: 5° C./min up to 150° C., hold 3.5 min Ramp 2: 5°/min up to 210° C. Ramp 3: 6° C./min up to 249° C. |

The chromatogram for this sample appears in FIG. 6. The peaks numbered from 1 to 9 correspond to the compounds as indicated in Table 1.

COMPARATIVE EXAMPLE 4

The sample in Example 3 was analyzed using the unmodified GC-MS system employed in Comparative Example 2, under the operating conditions reported in Table 2. The chromatogram for this sample appears in FIG. 7. The peaks numbered from 1 to 9 correspond to the compounds as indicated in Table 1.

The comparison between the chromatogram appearing in FIG. 6 and the chromatogram appearing in FIG. 7 reveals that the spectrum obtained using the GC-MS system according to the invention has better linearity and greater sensitivity.

The peak 1 for limonene remained nearly unchanged in both spectra, because, being a hydrocarbon having no heteroatoms, limonene has low reactivity to hydrogen.

Using the chromatogram of FIG. 7, the qualitative analysis of an unknown sample containing the substances indicated in Table 1 would be impossible, due to the alterations undergone by the mass spectra of the substances. In particular, from the chromatogram acquired on the unmodified GC-MS system, it would be impossible to assign peaks 3, 4 and 5 (corresponding to isobornyl acetate, styralyl acetate and benzyl acetate) correctly by comparison with the spectra in the literature (e.g. in the NIST Standard Reference Database).

Peaks 2, 6, 7, 8 and 9 (corresponding to benzoic aldehyde, 4-methoxybenzaldehyde, 4-Allyl-2-methoxyphenol, a-Hexylcinnamaldehyde and diethyl phthalate) exhibit considerable tails, which instead make it difficult to carry out a quantitative analysis based on the chromatogram of FIG. 7.

All peaks from 2 to 9 also have a much smaller area than the area of peak 1, in spite of the fact that the concentration of the relative substances in the sample is equal (or greater, in the case of substance no. 9) to that of substance no 1.

The defects indicated above prove to be mitigated to a great extent, if not eliminated, in the chromatogram appearing in FIG. 6, which was obtained according to the invention. FIG. 8(a) is an enlargement of a portion of the spectrum of FIG. 6 and FIG. 8(b) is an enlargement of FIG. 7. Mitigation of the tails and the increase in sensitivity, obtained using the GC-MS method and system according to the invention prove to be evident from the enlargements.

The invention claimed is:

1. A gas chromatograph-mass spectrometer, characterized in that the ion source of the mass spectrometer comprises an ionization chamber, wherein the internal surface of at least one wall of said ionization chamber has the chemical structure of at least one layer of graphene.

2. The gas chromatograph-mass spectrometer according to claim 1, wherein the ion source is selected from among an electron ionization (EI) ion source or a chemical ionization (CI) ion source.

3. The gas chromatograph-mass spectrometer according to claim 1, wherein the internal surface of all the walls of the ionization chamber has the chemical structure of at least one layer of graphene.

4. The gas chromatograph-mass spectrometer according to claim 1, wherein the internal surface of at least one wall of the ionization chamber has at least one layer of graphene deposited or grown on said surface.

5. The gas chromatograph-mass spectrometer according to claim 1, wherein the internal surface of at least one wall of the ionization chamber has the structure of graphite.

6. The gas chromatograph-mass spectrometer according to claim 5, wherein the graphite is selected from among crystalline flake graphite, microcrystalline graphite, expanded graphite, pyrolytic graphite and synthetic graphite.

7. The gas chromatograph-mass spectrometer according to claim 5, wherein at least one wall of the ionization chamber is entirely made up of graphite.

8. The gas chromatograph-mass spectrometer according to claim 5, wherein at least one wall of said ionization chamber has a multilayer structure comprising at least one external metallic layer and an internal layer of graphite.

9. The gas chromatograph-mass spectrometer according to claim 1, wherein the internal surface of at least one wall of the ionization chamber is covered with an insert, the internal surface of which has the chemical structure of at least one layer of graphene.

10. The gas chromatograph-mass spectrometer according to claim 9, wherein said insert is entirely made up of graphite.

11. The gas chromatograph-mass spectrometer according to claim 9, wherein said insert comprises an internal layer entirely made up of graphite and at least one external support coupled to said internal layer.

12. The gas chromatograph-mass spectrometer according to claim 9, wherein the internal surface of said insert has at least one layer of graphene deposited or grown on said surface.

13. The gas chromatograph-mass spectrometer according to claim 10, wherein the thickness of the wall of the insert is ≤2.5 mm.

14. The gas chromatograph-mass spectrometer according to claim 9, wherein said insert is formed by a number of pieces.

15. A gas chromatography-mass spectrometry method comprising the use of a gas chromatograph-mass spectrometer according to claim 1.

16. The gas chromatography-mass spectrometry method according to claim 15, comprising:
providing a first sample comprising a plurality of analytes;
providing a separation column comprising at least one stationary phase capable of selectively adsorbing at least one analyte;
introducing the first sample at one end of the separation column and enabling the sample to flow through the column, separating said plurality of analytes based on their affinity for said stationary phase, utilizing hydrogen as the carrier gas, thereby obtaining at least a second gaseous sample;
ionizing said second gaseous sample in the ion source of the mass spectrometer comprising an ionization chamber in which the internal surface of at least one wall of said ionization chamber has the chemical structure of at least one layer of graphene, thereby producing ions;
analyzing the ions produced based on the mass thereof.

17. The gas chromatography-mass spectrometry method according to claim 15, wherein the first gaseous sample comprises hydrogen and a plurality of analytes, wherein at least one of said analytes is selected from among hydrocarbons ranging from C1 to C50 and having at least one functional group that is reactive to hydrogen.

18. A mass spectrometry method comprising:
providing a gaseous sample comprising hydrogen and at least one analyte;
ionizing said gaseous sample in the ion source of the mass spectrometer of claim 1 comprising an ionization chamber in which the internal surface of at least one wall of said ionization chamber has the chemical structure of at least one layer of graphene, thereby producing ions;
analyzing the ions produced based on the mass thereof.

19. The gas chromatograph-mass spectrometer according to claim 8, wherein the at least one external metallic layer is made of stainless steel.

20. The gas chromatograph-mass spectrometer according to claim 13, wherein the thickness of the wall of the insert is in the range of from 0.4 mm to 1.5 mm.

* * * * *